United States Patent
Sato et al.

(10) Patent No.: US 7,749,013 B2
(45) Date of Patent: *Jul. 6, 2010

(54) BIOLOGICAL ELECTRODE AND CONNECTOR FOR THE SAME

(75) Inventors: Takanori Sato, Tokyo (JP); Yasuyuki Nonaka, Tokyo (JP); Hirohito Igarashi, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/187,001

(22) Filed: Jul. 22, 2005

(65) Prior Publication Data

US 2005/0255739 A1    Nov. 17, 2005

Related U.S. Application Data

(62) Division of application No. 10/638,331, filed on Aug. 12, 2003, now Pat. No. 7,085,598.

(30) Foreign Application Priority Data

Aug. 23, 2002   (JP)   ............... P2002-243957

(51) Int. Cl.
  *H01R 13/52*   (2006.01)
(52) U.S. Cl. ............. 439/281; 439/859; 439/909; 600/372
(58) Field of Classification Search ........... 439/281, 439/271, 859, 909; 600/372, 391, 392
See application file for complete search history.

(56) References Cited

U.S. PATENT DOCUMENTS

| | | | |
|---|---|---|---|
| 3,954,100 A | | 5/1976 | Sem-Jacobsen |
| 4,040,412 A | | 8/1977 | Sato |
| 4,051,842 A | * | 10/1977 | Hazel et al. ............... 600/391 |
| 4,166,465 A | * | 9/1979 | Esty et al. ................. 606/32 |
| 4,370,984 A | * | 2/1983 | Cartmell ................... 600/385 |
| 4,522,211 A | * | 6/1985 | Bare et al. ................ 600/392 |
| 4,637,399 A | | 1/1987 | Asai et al. |
| 4,776,350 A | * | 10/1988 | Grossman et al. .......... 607/152 |
| 4,915,656 A | * | 4/1990 | Alferness .................. 439/729 |
| 4,974,594 A | * | 12/1990 | Berlin ...................... 600/395 |
| 5,224,882 A | * | 7/1993 | Olms ....................... 439/725 |
| 5,947,897 A | | 9/1999 | Otake |
| 6,223,088 B1 | * | 4/2001 | Scharnberg et al. ........ 607/142 |
| 6,623,312 B2 | * | 9/2003 | Merry et al. .............. 439/729 |

FOREIGN PATENT DOCUMENTS

| | | |
|---|---|---|
| JP | 63-103604 | 7/1988 |
| JP | 1-48015 B2 | 10/1989 |
| JP | 8-317913 A | 12/1996 |
| JP | 2605272 Y2 | 4/2000 |

* cited by examiner

*Primary Examiner*—Xuong M Chung-Trans
(74) *Attorney, Agent, or Firm*—Sughrue Mion, PLLC

(57) ABSTRACT

A conductive member is adapted to be attached onto a living tissue to detect a bioelectrical signal. A retainer retains the conductive member on the living tissue. A lead member is partly brought into contact with the conductive member to lead out the bioelectrical signal to a connector. A waterproof sheet covers the lead member in a watertight manner, while exposing a portion of the lead member from which the biological signal is led out.

22 Claims, 9 Drawing Sheets

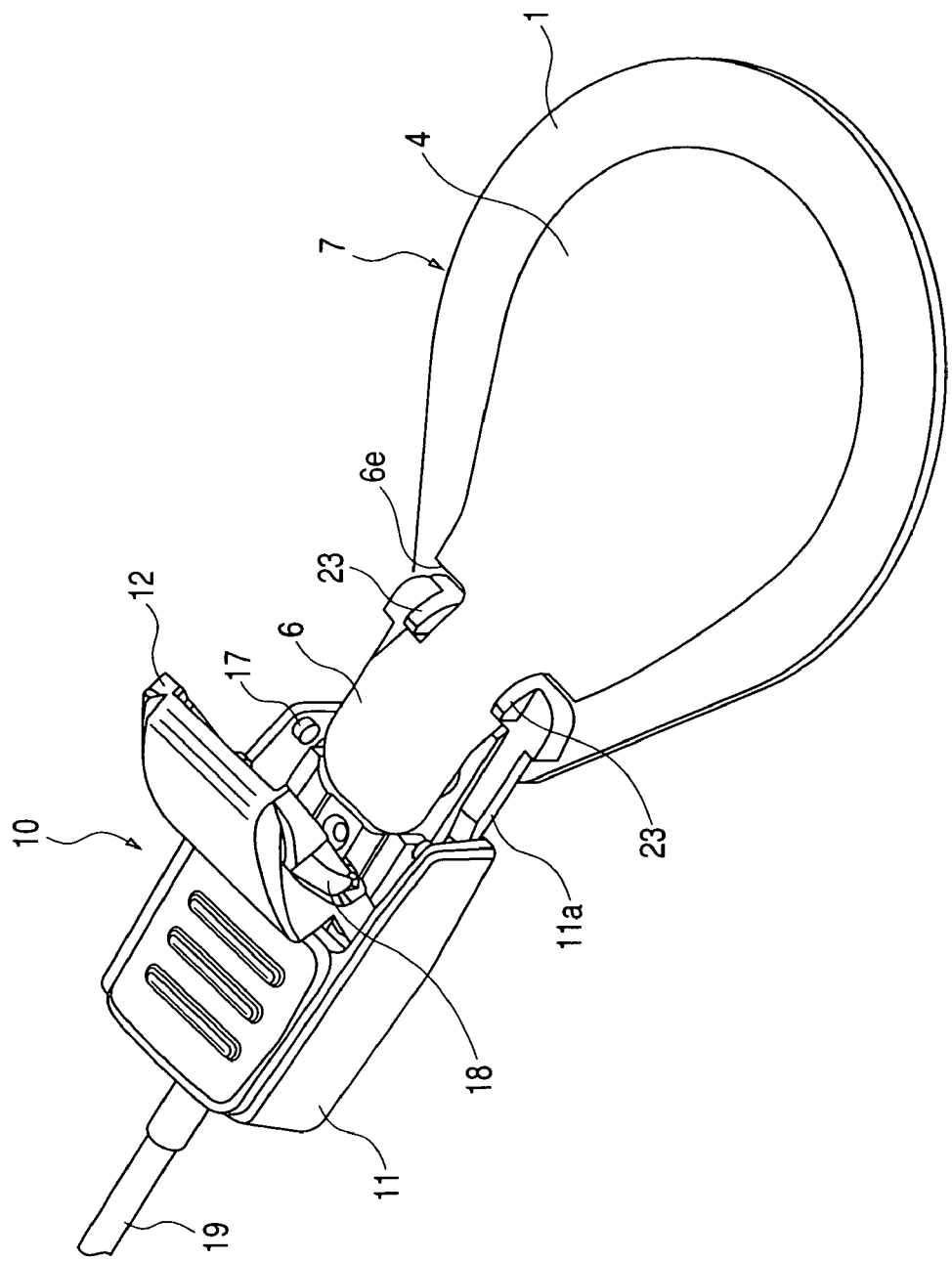

BIOLOGICAL ELECTRODE AND CONNECTOR FOR THE SAME

This is a divisional of application Ser. No. 10/638,331 filed Aug. 12, 2003 now U.S. Pat. No. 7,085,598. The entire disclosure is hereby incorporated by reference.

BACKGROUND OF THE INVENTION

The invention relates to a biological electrode for detecting an electrical signal of a living body, and to a connector for use with a biological electrode (hereinafter called a "biological electrode connector") for leading an electrical signal from the biological electrode. More particularly, the invention relates to a biological electrode and a biological electrode connector which have a superior waterproof characteristic.

An ambulatory ECG (electrocardiogram) recorder is known as a device for measuring an electrical vital-sign signal; for example, an electrocardiogram signal, over a relatively long time period. Biological electrodes are attached to the breast or the like of a subject, and an electrocardiogram signal to be measured is recorded by a portable ambulatory ECG recorder.

Since measurement and recording operations take a relatively long time period, while the ambulatory ECG recorder performs measurement, a subject has a desire for washing away, under a shower, the sweat that builds up in the course of daily life.

However, biological electrodes and biological electrode connectors of a conventional ambulatory ECG recorder have insufficient waterproof characteristics. When the subject showers, water moisture comes into contact with conductive portions of the electrodes and the connectors, thereby causing noise. For this reason, the subject is usually not allowed to shower. In order to permit the subject to shower, considerably-large waterproof seals are affixed to the biological electrodes from above, to thereby ensure the water resistance of the biological electrodes and that of the biological electrode connectors.

Affixing of such large-size seals poses limitations on a body surface to be subjected to the shower, and areas of the body surface covered with the waterproof seals become stuffy. Further, when the body is moved with the waterproof seals affixed thereon, the skin is stretched. Therefore, demand has arisen for a biological electrode and a biological electrode connector which enable a subject to shower without a necessity for affixing large waterproof seals to the body.

Biological electrodes and biological electrode connectors, both having waterproof characteristics, are disclosed in Japanese Patent Publication No. 1-48015B2. The biological electrode is formed by placing an electrode plate in a suction cup made of waterproof, elastic synthetic resin. When the suction cup is pressed from the outside, a contact sheet affixed to an internal surface of the suction cup comes into intimate contact with the body surface.

However, restoration force; that is, the force required by the suction cup to restore its original shape, is always exerted on the body surface. Hence, if the biological electrode is attached to a body surface for a long time period, there may arise a risk of inflammation of areas on the body surface where the contact sheet is to be attached. Further, the restoration force exerted on the body surface makes the subject feel uncomfortable.

Japanese Patent Publication No. 8-317913A discloses a device for measuring an electrocardiogram signal with a waterproof characteristic. A plurality of biological electrodes, a device for recording an electrical signal, and a battery are covered with a sheet-like waterproof base member in a watertight manner. An area on a body surface where the sheet-like base member is to be attached is large, and hence limitations are imposed on the body surface to be subjected to the shower, thus preventing the subject from being refreshed.

A related-art biological electrode connector is disclosed Japanese Utility Model Publication No. 2605272Y2. One side of each sheet-like conductive terminal of a biological electrode is provided with a conductive adhesive layer. A through hole is formed in an end portion of the terminal. A projecting section is provided at the extremity of a connector. The projecting section is inserted into the through hole, thereby electrically connecting the connector to the biological electrode. This configuration is superior, in that the connector is caught by the biological electrode without fail. However, a conductive portion in a connecting part between the electrode and the connector is exposed, thus failing to consider waterproofing.

SUMMARY OF THE INVENTION

It is therefore an object of the invention to provide a biological electrode and a connector for use with the biological electrode, wherein an area on a body surface where the biological electrode is to be attached is not large and waterproofing can be realized readily.

In order to achieve the above object, according to the invention, there is provided a biological electrode electrically connected to a connector, the biological electrode comprising:
a conductive member, adapted to be attached onto a living tissue to detect a bioelectrical signal;
a retainer, which retains the conductive member on the living tissue;
a lead member, partly brought into contact with the conductive member to lead out the bioelectrical signal to the connector; and
a waterproof sheet, covering the lead member in a watertight manner, while exposing a first portion of the lead member from which the biological signal is led out.

In such a configuration, a bioelectrical signal can be led to the connector from the waterproofed first portion.

Preferably, the lead member is plate-shaped, and the water proof sheet is laminated on both sides of the plate-shaped lead member.

In such a configuration, the waterproof reliability can be enhanced.

Preferably, the first portion is circular, so that the electrical contact between the biological electrode and the connector can be easily established.

Preferably, the biological electrode further comprises a protector, which prevents external vibrations from transmitting to the conductive member.

In such a configuration, it is prevented that vibrations are transmitted to the conductive member due to water droplets and water pressure of a shower, even when a subject takes the shower, thereby preventing occurrence of noise.

According to the invention, there is also provided a connector for a biological electrode which detects a bioelectric signal, the connector comprising:
a pair of nipping members, adapted to nip the biological electrode therebetween;
a conductive member, adapted to be brought into contact with a lead member of the biological electrode from which the detected bioelectric signal is led out; and
an elastic packing member, which waterproofs the conductive member, in a case where the nipping members nip the biological electrode.

In such a configuration, a portion of the lead member at which electrical connection is established can be waterproofed.

Preferably, the conductive member comprises a protrusion provided on one of the nipping members, and an indentation provided on the other one of the nipping members, into which the protrusion is fitted while nipping the lead member therebetween.

In such a configuration, the lead member is firmly nipped by the protrusion and the indentation.

Here, it is preferable that the protrusion has conductivity.

It is also preferable that: the protrusion is semi-spherical having a first curvature radius, and the indentation is semi-spherical having a second curvature radius smaller than the first curvature radius; and the indentation has elasticity.

In such a configuration, when the indentation having a relatively smaller curvature radius presses the lead member of the biological electrode against the protrusion, the lead member is pressed against the protrusion in a stretching manner by the elasticity of the indentation, and hence the lead member is nipped firmly.

Preferably, the elastic packing member annularly surrounds the protrusion.

Here, it is preferable that the connector further comprises an annular protrusion operable to push the elastic packing member outward, in a case where the protrusion is fitted into the indentation.

It is further preferable that an outer periphery of the annular protrusion is tapered.

It is further preferable that an inner periphery of the elastic packing member is tapered.

Alternatively, the annular protrusion may be operable to push the elastic packing member inward, in a case where the protrusion is fitted into the indentation. In this case, an inner periphery of the annular protrusion is tapered, and an outer periphery of the elastic packing member is tapered.

According to the invention, there is also provided a connector for a biological electrode which detects a bioelectric signal, the connector comprising:

a pair of nipping members, adapted to nip the biological electrode therebetween, one of the nipping members provided with a protrusion, and the other one of the nipping members provided with an indentation into which the protrusion is fitted while nipping therebetween a lead member of the biological electrode from which the detected bioelectric signal is led out.

According to the invention, there is also provided a connector for a biological electrode which detects a bioelectric signal, the connector comprising:

a pair of nipping members, adapted to nip the biological electrode therebetween;

an engagement member, adapted to be engaged with a lead member of the biological electrode from which the detected bioelectric signal is led out; and a conductive member, adapted to be brought into contact with the lead member, in a case where the engagement member engages with the lead member.

In such a configuration, the electric connection between the biological electrode and the connector can be easily and surely established.

BRIEF DESCRIPTION OF THE DRAWINGS

The above objects and advantages of the present invention will become more apparent by describing in detail preferred exemplary embodiments thereof with reference to the accompanying drawings, wherein:

FIG. 8 is a perspective view showing the way to cause the biological electrode connector to nip the biological electrode.

DETAILED DESCRIPTION OF THE INVENTION

Figure 1:
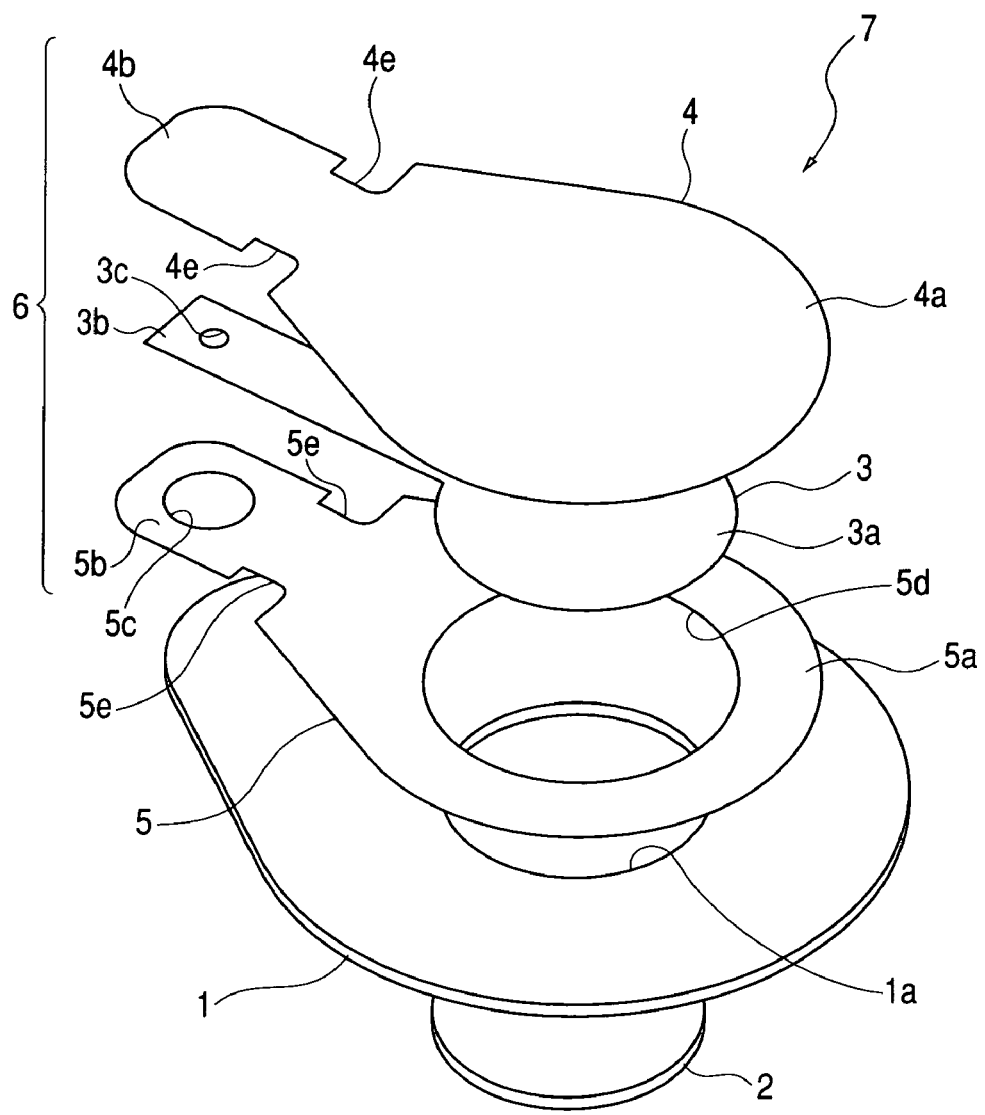
FIG. 1 is an exploded perspective view of a biological electrode according to a first embodiment of the invention.

In relation to the configuration of a biological electrode of the invention, a first embodiment will be described by reference to FIG. 1.

A biological electrode 7 is made up of a retainer 1, a conductive gel (conductive member) 2, a conductive lead 3, and waterproof sheets 4, 5.

The conductive gel 2 is brought into contact with a living tissue, to thereby detect an electrical signal. The conductive gel 2 is placed and retained in a hole 1a formed in the center of the retainer 1. The side of the retainer 1 to be brought into contact with a living tissue is given adhesion properties and attached to a living tissue. A raw material of the retainer 1 may be, e.g., polyolefin foam which has bioadaptability and a waterproof characteristic.

The conductive lead 3 is formed from an Ag/AgC sheet. A circular base 3a remains in contact with the conductive gel 2. As a result, the electrical signal of the living body detected by the conductive gel 2 is led to a lead section 3b of the conductive lead 3. A hole 3c is formed in the lead section 3b.

Materials of the waterproof sheets 4, 5 are non-conductive and have a waterproof characteristic. For example, the material may be a waterproof film, such as waterproof films which are easy to process and are made of PET, PV, PE, or PP. The waterproof sheet 4 is of size sufficient to cover the entire conductive lead 3 and is made up of a base 4a and an end section 4b. Notches 4e are formed between the base 4a and the end section 4b.

The waterproof sheet 5 is made up of a base 5a and an end section 5b, and a hole 5c is formed in the end section 5b. The hole 5c is larger in diameter than the hole 3c. Notches 5e are formed between the base 5a and the end section 5b. A hole 5d identical in size with the base 3a is formed in the base 5a such that the conductive gel 2 and the base 3a of the conductive lead 3 come into contact and electrical connection with each other.

The end section 5b of the waterproof sheet 5 and the end section 4b of the waterproof sheet 4 are identical in shape. An outer peripheral shape of the base 5a is identical with the outer peripheral shape of the base 4a. The waterproof sheets 4, 5 are laminated together while the conductive lead 3 is sandwiched therebetween. In this case, portions of the waterproof sheets 4, 5 which are identical in shape with each other and the notches 4e and 5e are laminated together without involvement of a displacement, thereby making the holes 3c and 5c concentric. Lamination may be realized by, e.g., welding or adhesion by a glue or adhesive.

The lamination 6 is formed from the waterproof sheets 4, 5 and the conductive lead 3. The base 3a is exposed on the side of the lamination 6 to be attached to the retainer 1 (i.e., the side of the lamination facing the waterproof sheet 5). A portion of the lead section 3b is exposed by way of the hole 5c.

The thus-exposed base 3a comes into contact with the conductive gel 2, to thereby lead out an electrical signal.

Of the base 5a of the waterproof sheet 5 of the lamination 6, a portion of the base 5a to come into contact with the retainer 1 is given a bonding characteristic and bonded to the retainer 1.

By such a configuration, the conductive gel 2 is held by the retainer 1 in a watertight manner when attached to a living tissue. Further, the portion of the conductive lead 3 exposed by way of the hole 5c is caught in a watertight manner by the connector that leads an electrical signal to the biological electrode connector. As a result, an electrical signal (e.g., an electrocardiogram signal) can be detected while the entirety of the biological electrode is held in a waterproof state.

Figure 2:
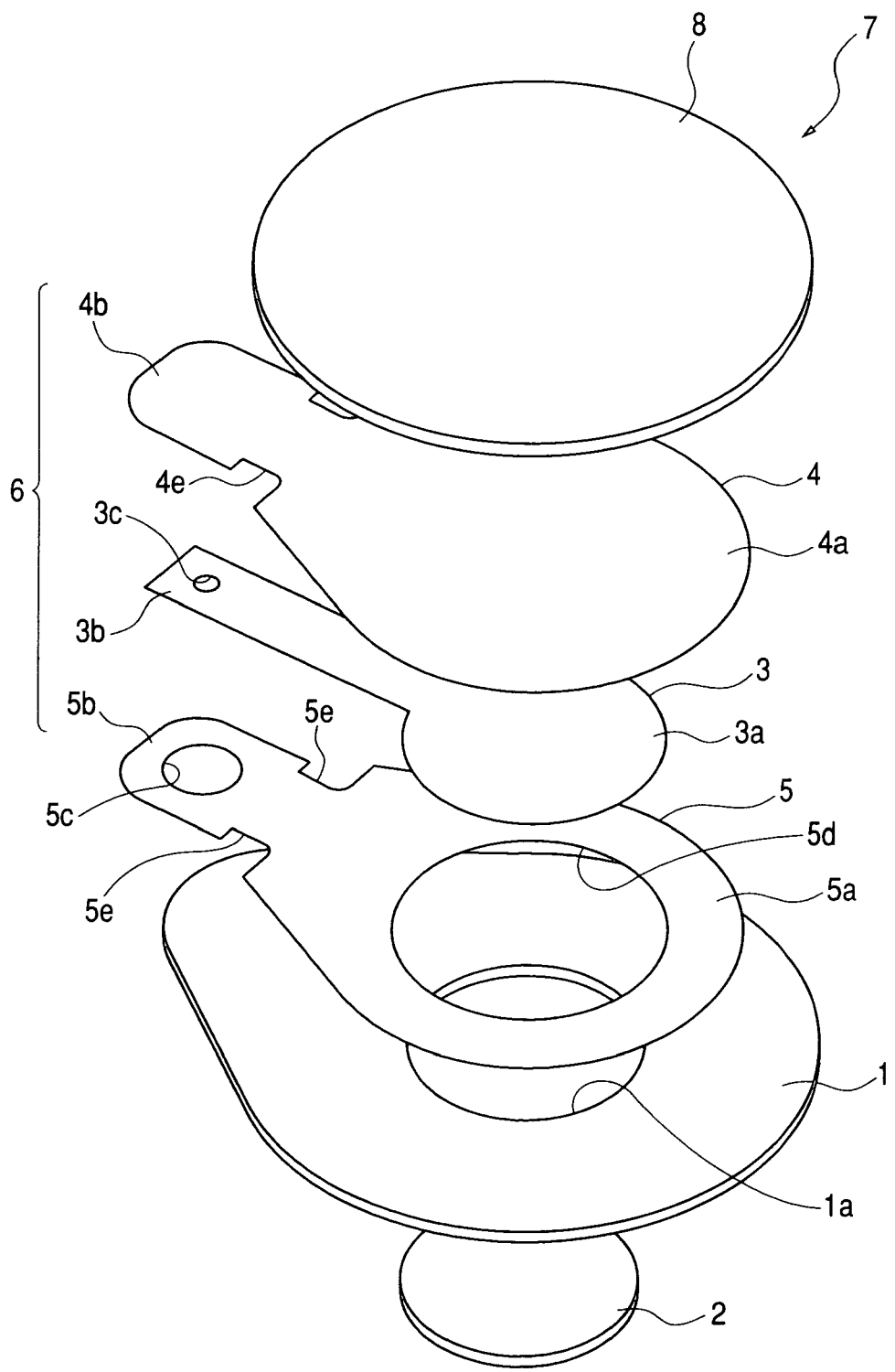
FIG. 2 is an exploded perspective view of a biological electrode according to a second embodiment of the invention.

In relation to the configuration of the biological electrode of the invention, a second embodiment will be described by reference to FIG. 2.

The biological electrode 7 is made up of the retainer 1, the conductive gel (conductive member) 2, the conductive lead 3, the waterproof sheets 4, 5, and a protector 8.

The retainer 1, the conductive gel (conductive member) 2, the conductive lead 3, and the waterproof sheets 4, 5 are the same as those described in connection with the first embodiment.

The role of the protector 8 is to prevent transmission of water pressure and vibration to the conductive gel 2 and the conductive lead 3, which would otherwise be caused by water droplets of the shower, so that an electrical signal (e.g., an electrocardiogram signal) can be detected while a subject is showering with the biological electrodes 7 attached to the surface of the subject's living body. If water pressure or vibration has been transmitted to the conductive gel 2 and the conductive lead 3, noise will arise in an electrical signal.

The protector 8 assumes a disk-shape and is bonded onto the base 4a of the waterproof sheet 4 by a glue or adhesive. A raw material may be material capable of preventing transmission of vibration to the conductive gel 2 or the conductive lead 3, which would otherwise be caused by water droplets of the shower; for example, polyolefin foam. The protector 8 is larger than at least the base 3a of the conductive lead 3. More preferably, the protector 8 is of size sufficient to cover the bases 4a, 5a of the waterproof sheets 4, 5.

Figure 3:
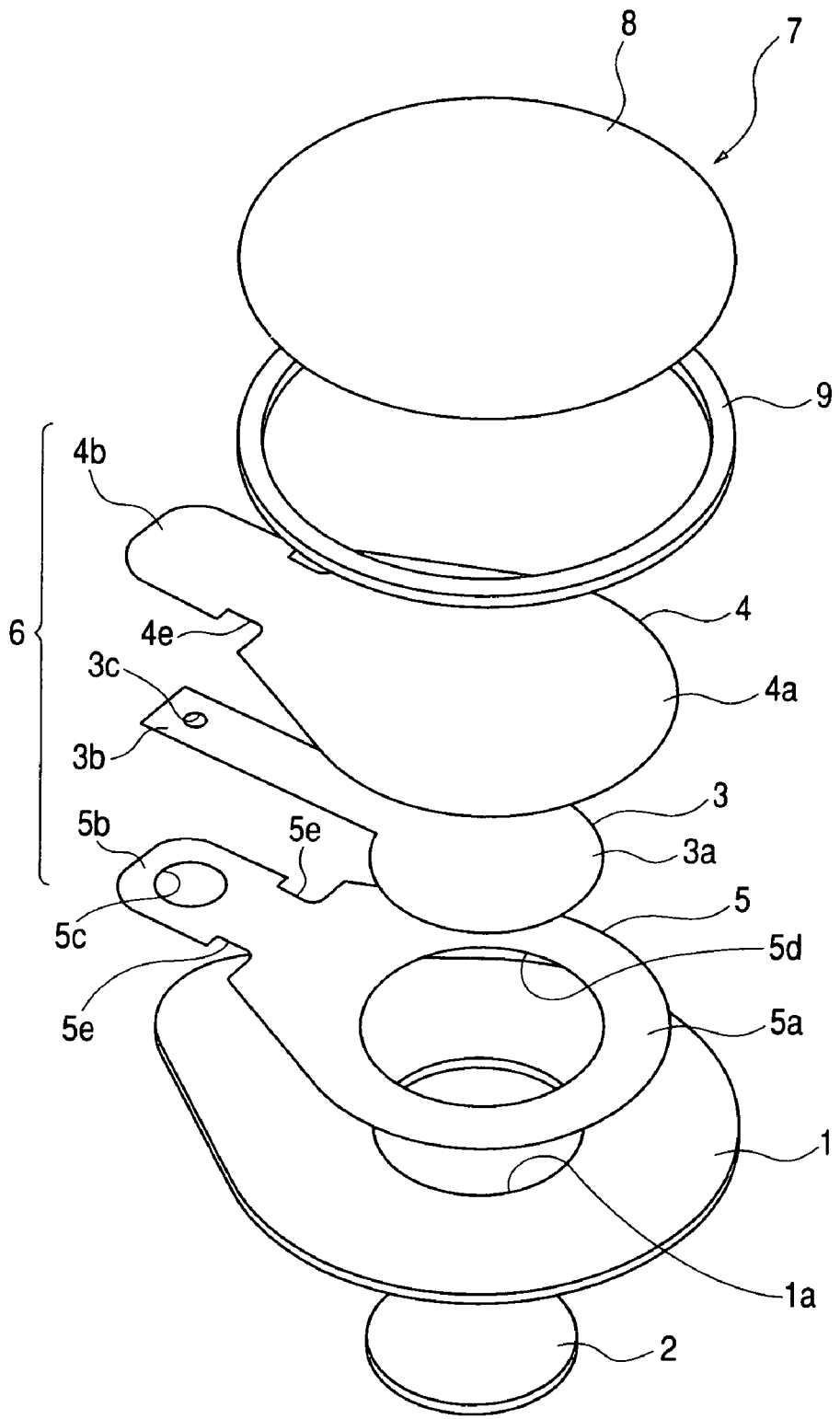
FIG. 3 is an exploded perspective view of a biological electrode according to a third embodiment of the invention.

In relation to the configuration of a biological electrode of the invention, a third embodiment will be described by reference to FIG. 3.

The third embodiment is an example in which the structure of the second embodiment for preventing occurrence of vibration, which would otherwise be caused by water droplets of the shower, has been reinforced.

Specifically, an annular reinforcement 9 whose outer peripheral diameter is identical with that of the circular protector 8 is interposed between the circular protector 8 and the waterproof sheet 4, both being described in connection with the second embodiment. The circular protector 8 and the annular reinforcement 9 are bonded to the base end section 4a by a glue or adhesive while their outer peripheries are aligned with each other. As in the case of the second embodiment, the circular protector 8 and the annular reinforcement 9 are preferably larger than at least the base 3a of the conductive lead 3. More preferably, the circular protector 8 and the annular reinforcement 9 are of size sufficient to cover the bases 4a, 5a of the waterproof sheets 4, 5. By such a structure and as a result of the annular reinforcement 9 being interposed between the circular protector 8 and the waterproof sheet 4, a clearance develops between them. Water pressure and vibration due to water droplets of a shower are not transmitted directly to the waterproof sheet 4, and hence the clearance is more suitable for preventing noise.

The structure of the biological electrode connector 10 of a lead cable compatible with the biological electrode will now be described by reference to FIGS. 4 through 8.

Both side sections of a nipping base 11a are retained slidably by guide rails 11b provided on a base 11, so that the nipping base 11a can be accommodated in the base 11 or drawn out therefrom. The nipping cover 12 is pivotable about a pivot shaft provided on a proximal end section of the nipping base 11a.

When the nipping base 11a is drawn to a predetermined position from the base 11, further withdrawal of the nipping base 11a is hindered by an unillustrated stopper. When the nipping cover 12 is closed while the nipping base 11a remains withdrawn to this predetermined position, a guide projection 17 provided on either inner side face of the base 11 enters one end 18a of a guide groove 18 formed on either outer side face of the nipping cover 12. More specifically, a cutout 18c is formed in the one end 18a of each of the guide grooves 18 in the nipping cover 12, and the guide projections 17 enter the guide grooves 18 by way of the cutouts 18c, respectively.

When the nipping base 11a is slid in a direction in which the nipping base 11a is to be accommodated into the base 11 along the guide rails 11b while the nipping cover 12 is closed, the guide projections 17 slide along the guide grooves 18 and travel toward the other ends 18b of the guide grooves 18, respectively.

The guide grooves 18 are formed so as to become spaced from the nipping base 11a with decreasing distance to the other ends 18b while the nipping cover 12 is closed. Therefore, when the nipping base 11a is moved in a direction in which the nipping base 11a is accommodated into the base 11, the guide projections 17 fitted into the guide grooves 18 are moved while pressing the sliding faces of the guide grooves 18 toward the nipping base 11a, because the nipping base 11a is supported by the guide rails 11b. Therefore, the nipping cover 12 becomes more firmly closed by the nipping base 11a. Predetermined portions (hereinafter, referred as locking portions) including the extremities of the other ends 18b of the guide grooves 18 are in parallel with the guide rails 11b whose positions are achieved when the nipping cover 12 is closed. Further, raised sections 18d are provided on the bottom surfaces of the respective guide grooves 18 at positions before the locking portions. The guide projections 17 enter the locking portions while pressing the raised sections 18d by the front end faces of the guide projections 17. The raised portions 18d are provided for preventing easy removal of the guide projections 17 from the locking portions. The guide projections 17 remaining in the guide grooves 18 prevent the nipping cover 12 from directly opening in this state. In this way, the nipping cover 12 is held in a closed state. When the nipping cover 12 is opened, the individual sections are actuated in the reverse procedure to the closing procedure.

Next, an electrical connection between the biological electrode 7 and the biological electrode connector 10 will be described. The nipping base 11a is provided with a conductive protrusion 13 having a semi spherical top, and an annular packing 14 provided concentrically with the protrusion 13. For instance, a rubber packing having elasticity is preferable for the packing 14. As will be described later, the protrusion 13 is electrically connected to the lead section 3b from which the biological electrode 7 is exposed.

Figure 5:
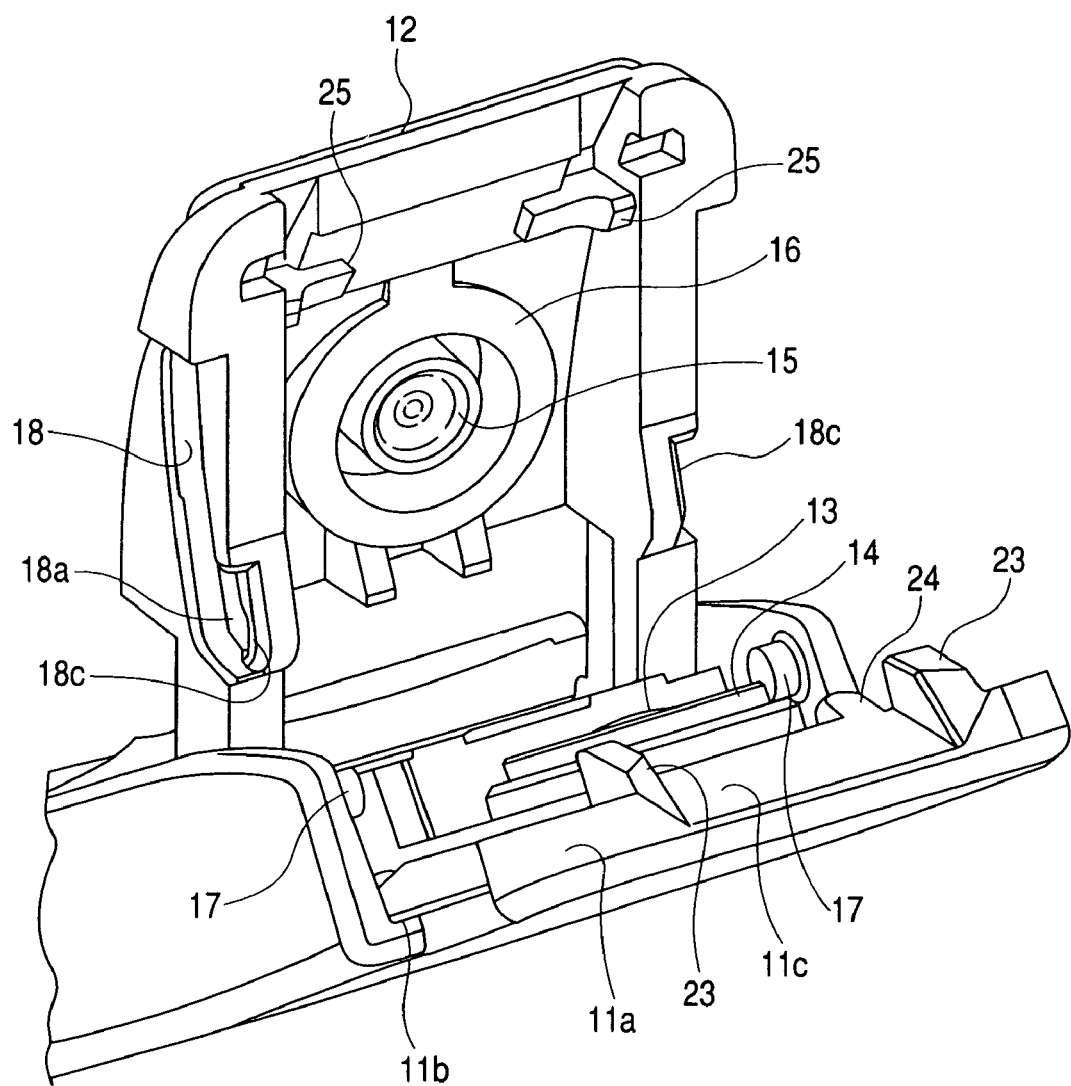
FIG. 5 is an enlarged perspective view of the biological electrode connector when viewed in the arrow A in FIG. 4.

As shown in FIG. 5, an indentation 15 and an annular protrusion 16 concentric therewith are provided on an inner side of the nipping cover 12. The indentation 15 may be, e.g., a rubber indentation having elasticity.

The diameter of the indentation 15 is made so as to become slightly smaller than that of the protrusion 13. A concave semi-spherical face of the indentation 15 is slightly smaller in curvature radius than the convex semi-spherical face of the protrusion 13.

Figure 6:
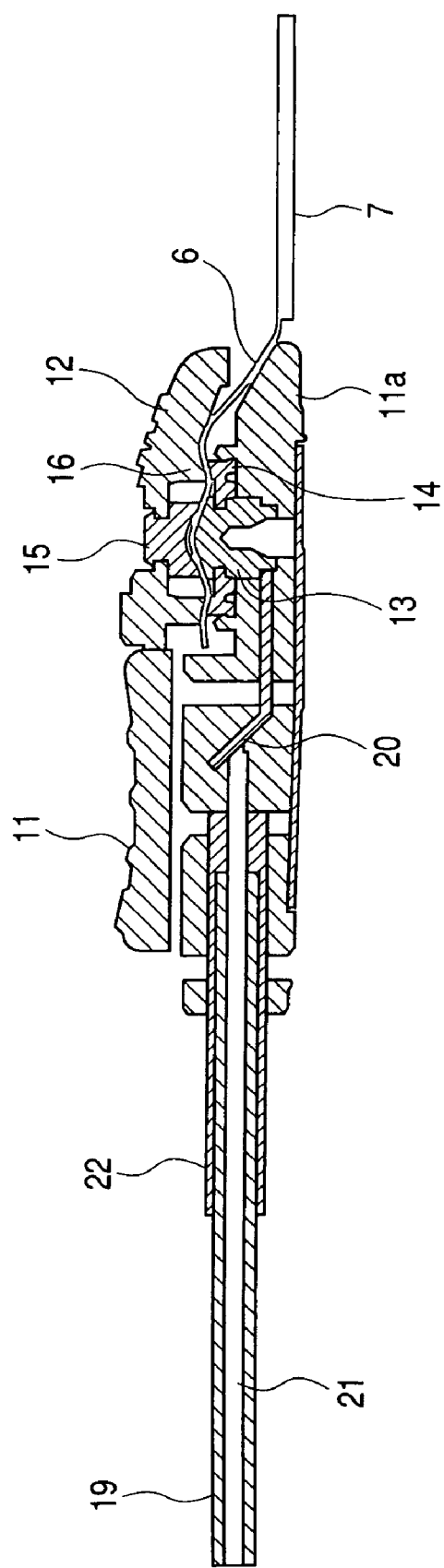
FIG. 6 is a longitudinal cross-sectional view of the biological electrode connector showing a state that the biological electrode is nipped.

FIG. 6 shows a cross-sectional view of the nipping cover 12 when the nipping cover 12 is closed so as to nip the lamination 6 of the biological electrode 7. As mentioned above, the protrusion 13 and the indentation 15 nip the lamination 6 in a concentric manner. The lamination 6 is nipped such that the hole 5c concentrically comes into contact with the protrusion 13. Therefore, the portion of the conductive lead 3 exposed by way of the hole 5c is electrically connected to the protrusion 13.

As mentioned above, the curvature radius of the concave semi-spherical face of the elastic indentation 15 is smaller than that of the convex semi-spherical face of the conductive, stiff protrusion 13. Therefore, when the conductive portion appearing from the hole 5c of the lamination 6 is pressed against the conductive protrusion 13, the electrical exposed portion is brought into frictional contact with the conductive protrusion 13 in a stretching manner by the elasticity of the indentation 15. Hence, the lamination 6 is firmly nipped, which in turn brings the conductive protrusion 13 and the exposed conductive portion into a superior electrically conductive state.

Incidentally, since the packing 14 is located so as to surround the electrical connection section, when the nipping cover 12 is closed, a watertight space is defined in a space between the nipping cover 12 and the nipping base 11a.

An outer periphery of a lower face of the annular protrusion 16 is tapered so that the annular protrusion easily pushes outward the annular packing 14 to realize smooth fitting between the annular protrusion 16 and the annular packing 14. An inner periphery of an upper face of the annular packing 14 may be tapered so as to conform with the tapered face of the annular protrusion 16 in order to nip the lamination 6 more firmly.

In the above case, the annular protrusion 16 is so configured as to deform the annular packing 14 entirely outward. In other words, the annular packing 14 is prevented from partly deformed outward while being partly deformed inward. In this respect, the annular protrusion 16 may be configured such that an inner periphery of the lower face thereof is tapered. In this case, an outer periphery of the upper face of the annular packing 14 may be tapered so as to conform with the tapered face of the annular protrusion 16.

The electrical signal which is detected by the biological electrode 7 and led to the conductive lead 3 travels through the protrusion 13 and a conductive plate 20, and is electrically led to a core 21 of a guide cable 19.

A portion of the guide cable 19 connected to the connector 10 is protected by a cable cover 22 in a watertight manner.

Figure 7A:
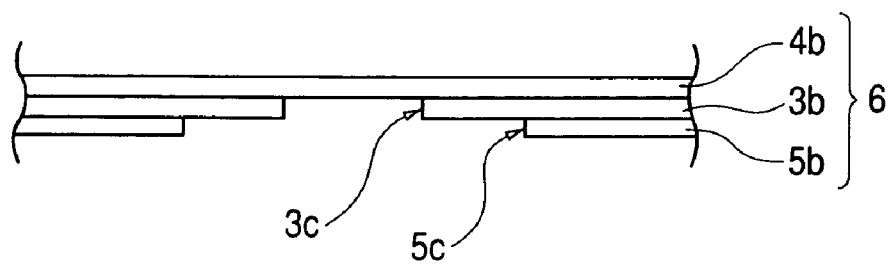
FIG. 7A is an enlarged cross-sectional view of the neighborhood of an area where a conductive lead of the biological electrode is exposed.
Figure 7B:
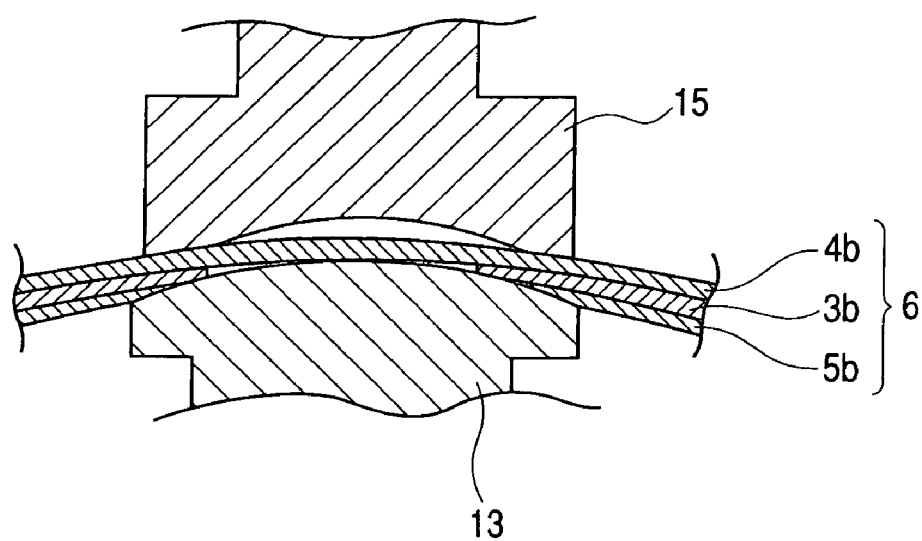
FIG. 7B is an enlarged cross-sectional view of the neighborhood of protrusion and indentation of the biological electrode connector, showing a state that the conductive lead of the biological electrode is nipped therebetween.

As shown in FIGS. 7A and 7B, the hole 5c from which the lead section 3b of the conductive lead 3 is exposed is designed so as to become smaller in diameter than the protrusion 13 and the indentation 15. Therefore, the exposed portion of the lead section 3b does not become exposed by way of the protrusion 13. By such a structure, the lead section 3b of the biological electrode 7 is electrically connected to the protrusion 13, whereby an electrical signal is led to the core 21 of the guide cable 19 by way of the conductive plate 20.

FIG. 8 is a view showing the method by which the biological electrode connector 10 is caused to nip the biological electrode 7. The lamination 6 of the biological electrode 7 is placed on the nipping base 11a such that notches 6e formed in the lamination 6 (i.e., an area where the notches 4e, 5e are laminated together) is engaged with engagement members 23 of the biological electrode connector 10. The nipping cover 12 is closed, to thereby accommodate the nipping base 11a into the base 11. As a result, as mentioned above, the exposed conductive section of the lamination 6 is electrically connected to the conductive projecting section. The biological electrode 7 and the biological electrode connector 10 are designed such that, when the notch 6e is engaged with the engagement members 23, the center of the hole 5c from which the exposed conductive section of the lamination 6 comes to the center of the protrusion 13. Therefore, the exposed conductive section of the lamination 6 comes into contact with the conductive protrusion 13 by simply engaging the notch 6e with the engagement members 23. Therefore, the exposed conductive section of the lamination 6 and the conductive protrusion 13 can be positioned easily without fail.

Figure 4:
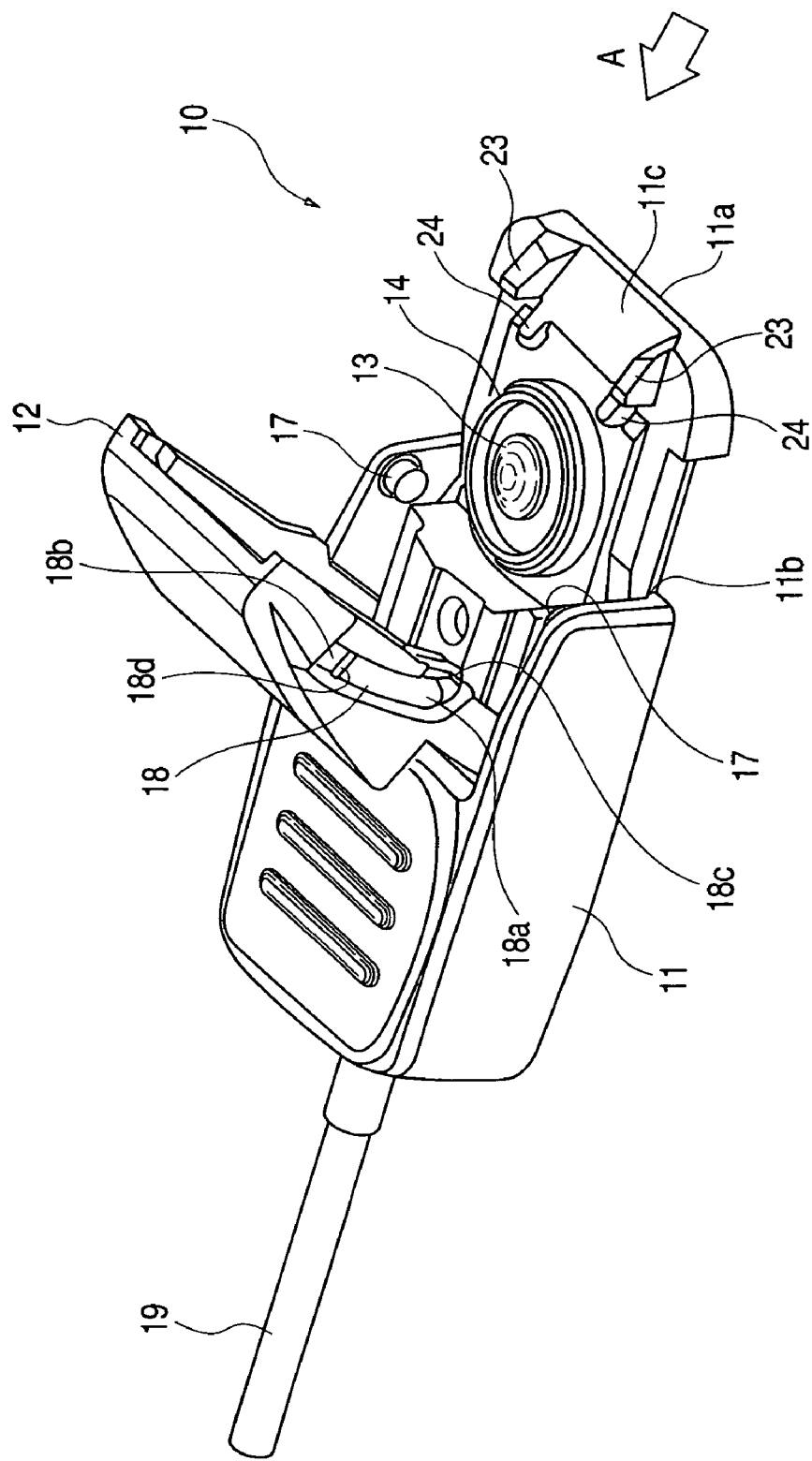
FIG. 4 is a perspective view of a biological electrode connector showing a state that a nipping cover is opened.

Further, FIG. 4 shows that the nipping base 11a has a slope portion 11c provided at the extremity of the nipping base 11a. Ribs 24, each having a face flush with the slope portion 11c, are provided at the nipping base 11a. FIG. 5 shows that rib receivers 25, each having faces which fit to an upper face and outer side faces of the rib 24, are provided at the inside of the nipping cover 12.

Figure 9:
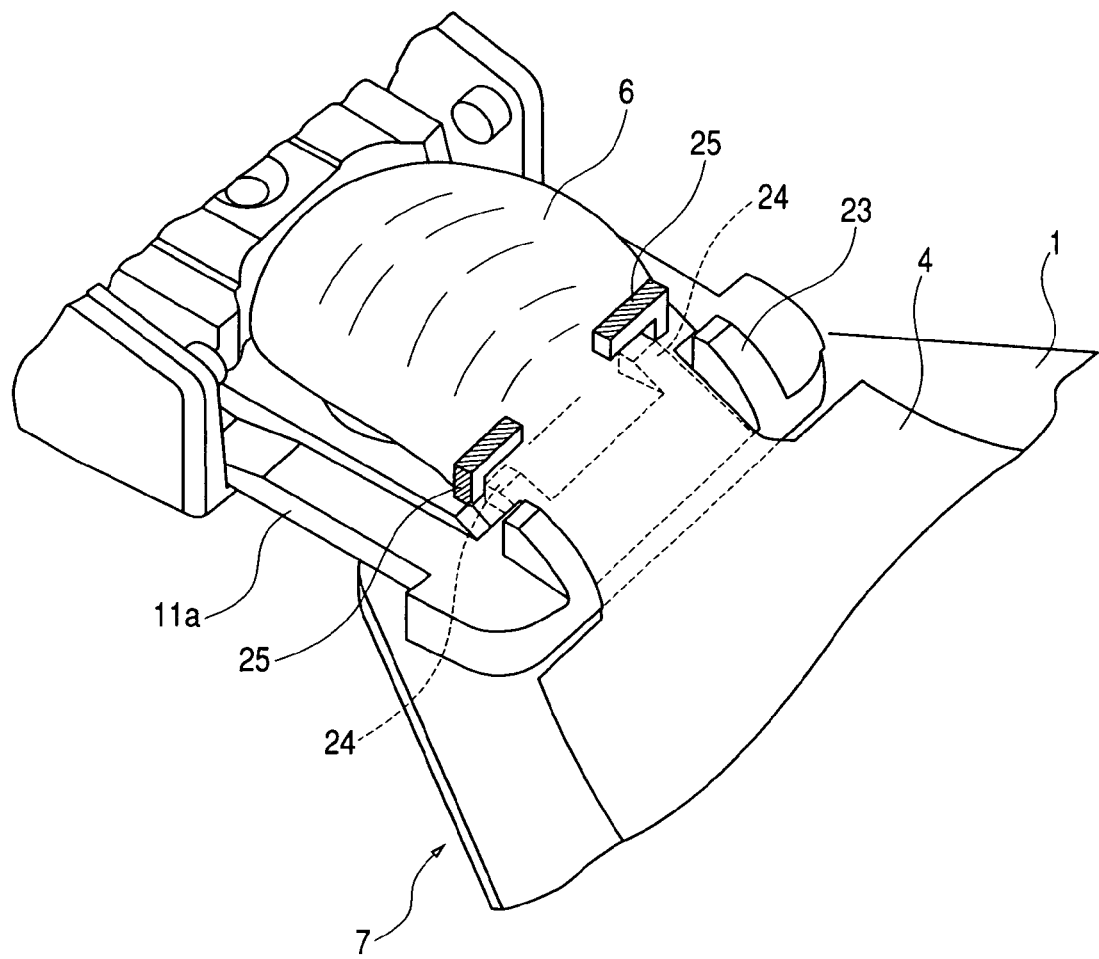
FIG. 9 is a perspective view of a lamination in the biological electrode, showing a state that the biological electrode is nipped by the biological electrode connector.

FIG. 9 is a view showing that the lamination 6 of the biological electrode 7 is nipped by the nipping base 11a and that, when the nipping cover 12 is closed, the rib receivers 25 are fit to the ribs 24 by way of the lamination 6. For the sake of convenience, the nipping cover 12 is not shown. Thus, as a result of the rib receivers 25 fitting to the ribs 24, the lamination 6 is subjected to a force which slightly raises and curves the center of the lamination 6, by the force exerted on the marginal portion of the lamination 6 where the rib receivers 25 and the ribs 24 come into contact with each other. The marginal portion of the lamination 6 is nipped by the rib receivers 25 and the ribs 24 while such force develops. Hence, when force is exerted on the biological electrode 7 for withdrawing the biological electrode 7, resistance withstands the developing force, thereby making withdrawal of the biological electrode 7 difficult. Further, as mentioned above, the exposed conductive section located in the vicinity of the center of the lamination 6 is vertically nipped between the conductive protrusion 13 and the indentation 15, whereby the lamination 6 is held firmly.

As mentioned above, the exposed portion of the lead section 3b by way of which the bioelectrical signal is led is electrically connected by the protrusion 13 of the connector 10 without fail. Further, the electrical connection between the exposed section of the lead section 3b and the protrusion 13 is held watertight by the packing 14. Further, a waterproof structure is established over a passage by way of which the electrical signal is led from the protrusion 13 to the core 21 of the guide cable 19.

As a result, the entire passage from the biological electrode 7 to the biological electrode connector 10 is made watertight.

Although the present invention has been shown and described with reference to specific preferred embodiments, various changes and modifications will be apparent to those skilled in the art from the teachings herein. Such changes and modifications as are obvious are deemed to come within the spirit, scope and contemplation of the invention as defined in the appended claims.

What is claimed is:

1. A connector for a biological electrode which detects a bioelectric signal, the connector comprising:
   a pair of nipping members, adapted to nip the biological electrode therebetween;
   a conductive member, adapted to be brought into contact with a lead member of the biological electrode from which the detected bioelectric signal is led out; and
   an elastic packing member, which waterproofs a space defined between the nipping members and at which the conductive member is brought into contact with the lead member so that the space is watertight, in a case where the nipping members nip the biological electrode,
   wherein:
   the conductive member comprises a protrusion provided on one of the nipping members, and an indentation provided on the other one of the nipping members, into which the protrusion is fitted;
   the lead member is nipped between the protrusion and the indentation; and
   a portion of the biological electrode is nipped between the indentation and the protrusion such that the indentation and the protrusion are separated from contacting one another by the portion of the biological electrode disposed therebetween.

2. The connector as set forth in claim 1, wherein the protrusion has conductivity.

3. The connector as set forth in claim 1, wherein:
   the protrusion is semi-spherical having a first curvature radius, and the indentation is semi-spherical having a second curvature radius smaller than the first curvature radius; and
   the indentation has elasticity.

4. The connector as set forth in claim 1, wherein ends of the protrusion and the indentation are disposed in the watertight space.

5. The connector as set forth in claim 1, wherein the elastic packing member annularly surrounds the protrusion.

6. The connector as set forth in claim 5, further comprising an annular protrusion operable to push the elastic packing member outward, in a case where the protrusion is fitted into the indentation.

7. The connector as set forth in claim 6, wherein an outer periphery of the annular protrusion is tapered.

8. The connector as set forth in claim 7, wherein an inner periphery of the elastic packing member is tapered.

9. The connector as set forth in claim 5, further comprising an annular protrusion operable to push the elastic packing member inward, in a case where the protrusion is fitted into the indentation.

10. The connector as set forth in claim 9, wherein an inner periphery of the annular protrusion is tapered.

11. The connector as set forth in claim 10, wherein an outer periphery of the elastic packing member is tapered.

12. A connector, configured to be connected to a biological electrode which is adapted to detect a biological signal, the connector comprising:
    a first nipping member and a second nipping member, adapted to nip the biological electrode therebetween;
    a protrusion, formed on the first nipping member;
    an indentation, formed on the second nipping member; and
    a conductive member, provided on the protrusion and adapted to contact, at an area between the protrusion and the indentation, a lead member of the biological electrode from which the detected biological signal is led out,
    wherein the protrusion and the indentation are configured to be separated from contacting one another by the lead member.

13. The connector as set forth in claim 12, wherein:
    the area is a watertight space bounded by an elastic packing member provided on one of the first nipping member and the second nipping member.

14. The connector as set forth in claim 12, wherein:
    the protrusion is semi-spherical having a first curvature radius; and
    the indentation is semi-spherical having a second curvature radius smaller than the first curvature radius.

15. The connector as set forth in claim 12, further comprising:
    an elastic packing member, which waterproofs the area when the first nipping member and the second nipping member nip the biological electrode.

16. The connector as set forth in claim 15, wherein:
    the elastic packing member annularly surrounds the protrusion.

17. The connector as set forth in claim 16, further comprising:
    an annular protrusion, configured to push the elastic packing member outward when the protrusion is fitted into the indentation.

18. The connector as set forth in claim 17, wherein:
    an outer periphery of the annular protrusion is tapered.

19. The connector as set forth in claim 18, wherein:
    an inner periphery of the elastic packing member is tapered.

20. The connector as set forth in claim 16, further comprising:
    an annular protrusion, configured to push the elastic packing member inward when the protrusion is fitted into the indentation.

21. The connector as set forth in claim 20, wherein:
    an outer periphery of the annular protrusion is tapered.

22. The connector as set forth in claim 21, wherein:
    an inner periphery of the elastic packing member is tapered.

* * * * *